US009358115B2

(12) United States Patent
Slater et al.

(10) Patent No.: US 9,358,115 B2
(45) Date of Patent: Jun. 7, 2016

(54) ARTIFICIAL HIP JOINT STEM AND ARTIFICIAL HIP JOINT INCLUDING THE SAME

(71) Applicant: KYOCERA Medical Corporation, Osaka-shi, Osaka (JP)

(72) Inventors: Nicholas Slater, Chandler, AZ (US); Takatoshi Miyashita, Hirakata (JP); Atsushi Kuroshima, Nara (JP); Shion Fujimura, Osaka (JP)

(73) Assignee: Kyocera Medical Corporation, Osaka (JP)

( * ) Notice: Subject to any disclaimer, the term of this patent is extended or adjusted under 35 U.S.C. 154(b) by 31 days.

(21) Appl. No.: 14/154,842

(22) Filed: Jan. 14, 2014

(65) Prior Publication Data

US 2015/0196397 A1    Jul. 16, 2015

(51) Int. Cl.
*A61F 2/30* (2006.01)
*A61F 2/36* (2006.01)

(52) U.S. Cl.
CPC ............ *A61F 2/3662* (2013.01); *A61F 2/30771* (2013.01); *A61F 2/367* (2013.01); *A61F 2/3672* (2013.01); *A61F 2/3676* (2013.01); *A61F 2002/30028* (2013.01); *A61F 2002/3082* (2013.01); *A61F 2002/30321* (2013.01); *A61F 2002/30906* (2013.01)

(58) Field of Classification Search
CPC ..... A61F 2/3662; A61F 2/3676; A61F 2/367; A61F 2202/3662; A61F 2202/366; A61F 2002/3668; A61F 2/3672; A61F 2/30771; A61F 2002/3664; A61F 2002/3666; A61F 2002/30321; A61F 2002/30028; A61F 2002/30906
See application file for complete search history.

(56) References Cited

U.S. PATENT DOCUMENTS

| | | | | | |
|---|---|---|---|---|---|
| 5,152,799 | A | * | 10/1992 | Lyons | A61F 2/3676 623/23.32 |
| 5,156,627 | A | * | 10/1992 | Amstutz | A61F 2/30767 623/22.41 |
| 5,443,523 | A | * | 8/1995 | Mikhail | A61F 2/30724 623/23.37 |
| 5,514,184 | A | * | 5/1996 | Doi | A61F 2/30767 623/23.3 |
| 6,193,761 | B1 | * | 2/2001 | Treacy | A61F 2/30767 433/201.1 |
| 6,395,327 | B1 | * | 5/2002 | Shetty | A61F 2/30767 427/190 |
| 7,323,013 | B2 | * | 1/2008 | McTighe | A61F 2/30767 623/23.29 |
| 2001/0039454 | A1 | * | 11/2001 | Ricci | A61B 17/68 623/23.5 |
| 2003/0074079 | A1 | * | 4/2003 | McTighe | A61F 2/30767 623/22.42 |
| 2006/0190092 | A1 | * | 8/2006 | Fridshtand | A61F 2/30767 623/23.35 |
| 2009/0299485 | A1 | * | 12/2009 | Michelinakis | A61F 2/30771 623/23.36 |
| 2012/0265319 | A1 | * | 10/2012 | Prybyla | A61F 2/34 623/22.36 |
| 2015/0173908 | A1 | * | 6/2015 | Shimozono | A61F 2/30907 623/20.36 |

OTHER PUBLICATIONS

Yamamuro, T., et al., "Bone Bonding Behavior of Biomaterials with Different Surface Characteristics under Load-Bearing Conditions", 1991, pp. 407-414. In the US: Devies, J. E., "The Bone-Biomaterial Interface", University of Toronto Press, 1991,10 pages.

* cited by examiner

*Primary Examiner* — Yashita Sharma
*Assistant Examiner* — Christie Bahena
(74) *Attorney, Agent, or Firm* — Volpe and Koenig, P.C.

(57) ABSTRACT

An artificial hip joint stem of the present invention includes a stem body divided into a stem proximal part, a stem distal part, and a stem intermediate part located between the stem proximal part and the stem distal part. The stem body includes a rough surface located at the stem proximal part and having a surface roughness (Ra) of 10-80 µm, a smooth satin surface located at the stem intermediate part and having a surface roughness (Ra) of 0.1-1.0 µm, and a shiny surface located at the stem distal part and having a surface roughness (Ra) of less than 0.1 µm. The present invention also provides an artificial hip joint including the artificial hip joint stem.

9 Claims, 11 Drawing Sheets

ARTIFICIAL HIP JOINT STEM AND ARTIFICIAL HIP JOINT INCLUDING THE SAME

FIELD OF INVENTION

The present invention relates to an artificial hip joint stem fixed to a femoral bone and an artificial hip joint including the artificial hip joint stem.

BACKGROUND ART

In order to restore the function of a hip joint deteriorated by disease or injury due to an accident or the like, hip replacement arthroplasty for replacing the hip joint with an artificial hip joint has been carried out conventionally. An artificial hip joint stem (hereinafter generally referred to as "stem") among members constituting the artificial hip joint is the substantially rod-shaped curved member inserted and fixed to a proximal part of the femoral bone.

The stem is classified into a stem using cement and a stem using no cement (hereinafter generally referred to as "cementless stem") according to a method of fixing the stem to the femoral bone. As the cementless stem, a bone preservation type stem that reduces injury to the femoral bone and its surrounding tissues has received attention in recent years. Examples of the bone preservation type stem include a type that reduces incisions of the proximal part of the femoral bone, muscles and ligaments by improving insertability of the stem, and a type that reduces the amount of removal of a cancellous bone and reduces injury to bone tissue by devising fixability of the stem.

On the other hand, techniques have been known which improve bonding strength between the stem and the bone by increasing a surface roughness (Ra) in order to roughen the surface of the stem (for example, refer to non patent document 1).

However, an increase in the surface roughness (Ra) of the stem increases friction against the bone. Therefore, when inserting the stem, a distal part of the stem is easy to contact with soft tissue and the cancellous bone at the proximal part of the femoral bone, resulting in poor insertability of the stem. The increase in the surface roughness (Ra) also facilitates bone ongrowth in which bone formation occurs on the surface of the stem, and hence the distal part of the stem is apt to be fixed to the femoral bone. Once the distal part of the stem is fixed to the femoral bone, there is possibility of occurrence of thigh pain and stress shielding in which bone density decreases and the bone shrinks due to less load applied to the bone.

PRIOR ART

Non Patent Document

Non patent document 1: J. E. Devies, "The Bone-Biomaterial Interface," (the USA), University of Toronto Press, 1991, pp. 407-414

SUMMARY

An object of the present invention is to provide an artificial hip joint stem having excellent stem insertability and capable of preventing the distal part of the stem from being fixed to the femoral bone, as well as an artificial hip joint including the artificial hip joint stem.

The artificial hip joint stem of the present invention includes a stem body divided into a stem proximal part, a stem distal part, and a stem intermediate part located between the stem proximal part and the stem distal part. The stem body includes a rough surface located at the stem proximal part and having a surface roughness (Ra) of 10-80 μm, a smooth satin surface located at the stem intermediate part and having a surface roughness (Ra) of 0.1-1.0 μm, and a shiny surface located at the stem distal part and having a surface roughness (Ra) of less than 0.1 μm.

The artificial hip joint of the present invention includes: the artificial hip joint stem of the present invention further including a neck part extending from a proximal end portion of the stem proximal part; an artificial femoral head (a metal or ceramic femoral head) fitted into the neck part; and a socket for slidably housing the artificial femoral head.

The present invention produces the effects of exhibiting the excellent stem insertability and preventing the distal part of the stem from being fixed to the femoral bone.

BRIEF DESCRIPTION OF THE DRAWINGS

FIGS. 1, 2, 5, 7 and 10 among FIGS. 1 to 11B show a state that the stem is implanted in a left leg. When the stem is implanted in a right leg, the latter is merely in a laterally line-symmetric relationship with the former.

DETAILED DESCRIPTION

Artificial Hip Joint Stem and Artificial Hip Joint
(First Embodiment)

An artificial hip joint stem and an artificial hip joint according to a first embodiment of the present invention are described in details below with reference to FIGS. 1 to 4C. Although the following description is made taking as an example the case of implanting the stem in the left leg, the stem of the present invention can also be implanted in a right leg.

Figure 1:
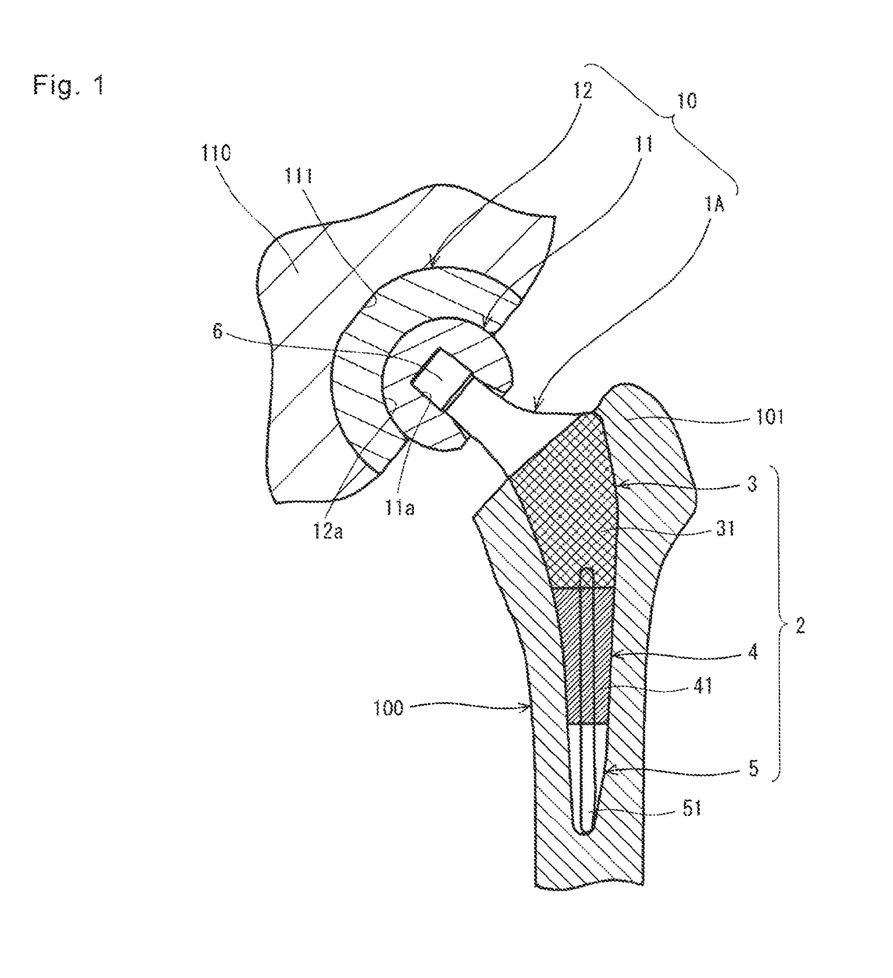
FIG. 1 is a schematic explanatory drawing of an artificial hip joint according to a first embodiment of the present invention.

As shown in FIG. 1, the artificial hip joint stem 1A of the present embodiment is the substantially rod-shaped curved member and constitutes the artificial hip joint 10. The stem 1A includes a stem body 2. The stem body 2 of the present embodiment is divided into a stem proximal part 3 located at a proximal part, a stem distal part 5 located at a distal part, and a stem intermediate part 4 located between the stem proximal part 3 and the stem distal part 5.

The phrase "proximal part" denotes the part located more closer to the head of a human body than an object to compare upon implantation of the artificial hip joint 10. The phrase "distal part" denotes the part located farther away from the head of the human body than the object to compare upon implantation of the artificial hip joint 10. In other words, the distal part is located closer to the toe tip of the human body.

Figure 2:
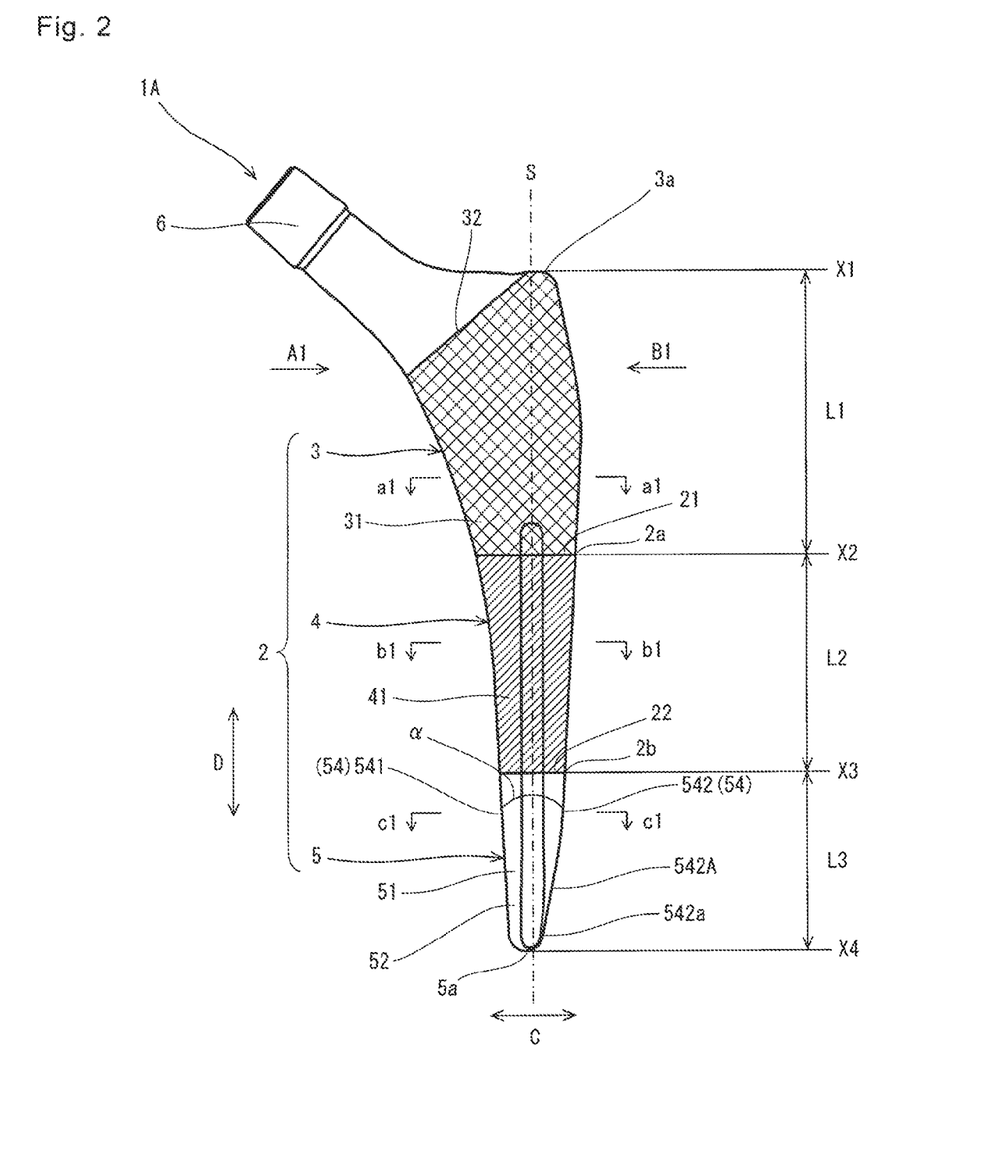
FIG. 2 is an enlarged front view showing an artificial hip joint stem according to the first embodiment of the present invention included in the artificial hip joint in FIG. 1.

The stem body 2 of the present embodiment includes a rough surface 31 located at the stem proximal part 3, a smooth satin surface 41 located at the stem intermediate part 4, and a shiny surface 51 located at the stem distal part 5. The rough surface 31 has a surface roughness (Ra) of 10-80 μm, preferably 20-80 μm, more preferably 30-70 μm. The smooth satin surface 41 has a surface roughness (Ra) of 0.1-1.0 μm. The shiny surface 51 has a surface roughness (Ra) of less than 0.1 μm, preferably 0.0 μm or more, less than 0.1 μm. This configuration provides the following effects.

That is, the stem 1A of the present embodiment is the member inserted from the stem distal part 5 and fixed to a proximal part 101 of the femoral bone 100. The stem body 2 of the stem 1A of the present embodiment includes the shiny surface 51 located at the stem distal part 5, and hence the stem distal part 5 is subjected to small friction against the bone. It is therefore capable of preventing the stem distal part 5 from being contacted with the soft tissue and the cancellous bone at the proximal part 101 of the femoral bone 100 when inserting the stem 1A, and consequently exhibiting the excellent stem insertability.

Additionally, the surface area of the stem distal part 5 is decreased by disposing the shiny surface 51 at the stem distal part 5. Consequently, the bone ongrowth is difficult to occur at the stem distal part 5, thus decreasing the contact area of the stem distal part 5 with respect to the medullary cavity of the femoral bone 100. Furthermore, the friction of the stem distal part 5 against the bone is decreased by disposing the shiny surface 51 at the stem distal part 5, thus reducing damage to the bone. This makes it possible to prevent the stem distal part 5 from being fixed to the femoral bone 100, thereby reducing the occurrence of the thigh pain and the stress shielding.

The stem 1A of the present invention is also capable of facilitating the bone ongrowth at the stem proximal part 3 because the stem body 2 has the rough surface 31 located at the stem proximal part 3, thereby enhancing the fixability of the stem 1A to the femoral bone 100. The stem 1A of the present invention is also capable of improving rotary resistance force of the stem 1A because the stem body 2 has the smooth satin surface 41 located at the stem intermediate part 4. As a result, it is capable of reducing the probability that when the stem 1A is subjected to load in a rotary direction, friction occurs against the bone and the stem 1A is subjected to rotary movement. The stem 1A of the present embodiment having these effects is suitable for use as the foregoing bone preservation type stem.

The rough surface 31 can be formed by, for example, titanium spraying or the like. The smooth satin surface 41 can be formed by, for example, blasting or the like. The shiny surface 51 can be formed by, for example, mirror surface processing or the like. The surface roughness (Ra) is the value measured according to JIS B 0633: 2001 (ISO 4288: 1996).

In the present embodiment, as shown in FIGS. 2, 3A, 3B and 4C, the stem body 2 further includes a front surface 52, a rear surface 53 and a side surface 54, each of which is located at the stem distal part 5. The front surface 52 is located on a front side of the stem distal part 5, and the rear surface 53 is located on a rear side of the stem distal part 5. The phrase "front side" denotes the side located along a direction in which the face of a human body is oriented upon implantation of the artificial hip joint 10. The phrase "rear side" denotes the side located along a direction in which the back of the human body is oriented upon implantation of the artificial hip joint 10. FIG. 2 shows the state that the stem 1A is implanted in the left leg. On the other hand, when the stem 1A is implanted in the right leg, the front surface 52 is located on the rear side of the human body, and the rear surface 53 is located on the front side of the human body.

The side surface 54 of the present embodiment includes an medial side surface 541 and an lateral side surface 542 opposed to each other. The medial side surface 541 is located on an medial side of the stem distal part 5, and the lateral side surface 542 is located on an lateral side of the stem distal part 5. The phrase "medial side" denotes a region located on a side closer to the centerline of the human body than the object to compare upon implantation of the artificial hip joint 10. The phrase "lateral side" denotes a region located on a side farther away from the centerline of the human body than the object to compare upon implantation of the artificial hip joint 10. FIG. 2 shows the state that the stem 1A is implanted in the left leg. Also, when the stem 1A is implanted in the right leg, the medial side surface 541 is located on the medial side of the human body, and the lateral side surface 542 is located on the lateral side of the human body.

In the present embodiment, the shiny surface 51 is located on the front surface 52, the rear surface 53 and the side surface 54. In other words, in the present embodiment, the shiny surface 51 is located over the entire circumference of the stem distal part 5. This configuration ensures well-balanced attainment of the foregoing effect owing to the shiny surface 51.

The present embodiment includes the following configuration from the viewpoint of well-balanced attainment of the foregoing individual effects owing to the rough surface 31 and the smooth satin surface 41. That is, the rough surface 31 is located over the entire circumference of the stem proximal part 3, and the smooth satin surface 41 is located over the entire circumference of the stem intermediate part 4 in the present embodiment.

In the present embodiment, as shown in FIG. 2, a first boundary part 21 of the rough surface 31 and the smooth satin surface 41 is substantially perpendicular to a central axis S of the stem body 2 in a front view. Similarly, a second boundary part 22 of the smooth satin surface 41 and the shiny surface 51 is substantially perpendicular to the central axis S of the stem body 2 in the front view. These configurations ensure well-balanced attainment of the foregoing individual effects owing to the rough surface 31, the smooth satin surface 41 and the shiny surface 51.

The phrase "front view" denotes a state of the stem 1A when the human body with the artificial hip joint 10 implanted in the left leg or right leg is viewed from the front side. The central axis S in the present embodiment corresponds to a bisector of an angle a formed by the medial side surface 541 and the lateral side surface 542 which are located at the stem distal part 5 and are opposed to each other. In the present embodiment, the distance between the medial side surface 541 and the lateral side surface 542 is decreased as going toward a distal end portion 5a of the stem distal part 5. When the medial side surface 541 and the lateral side surface 542 are parallel to each other, a configuration, which allows a midpoint in a width direction C at the stem distal part 5 to be continuously obtained along a longitudinal direction D of the stem body 2, is taken as the central axis S. Also in the present embodiment, the lateral side surface 542 has an inclined surface 542A as described later. When the lateral side surface 542 has the inclined surface 542A as in the present embodiment, the lateral side surface 542 employed in determining the central axis S is to be based on the configuration without the inclined surface 542A.

Figure 3A:
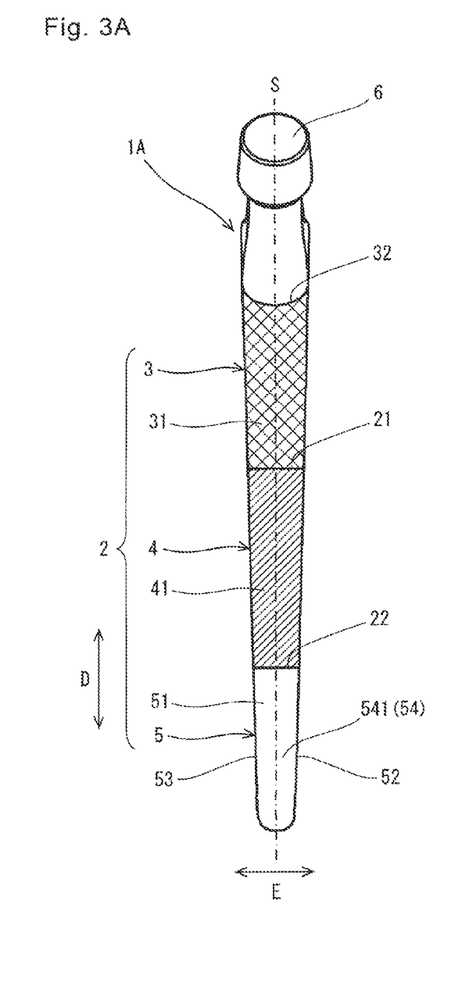
FIG. 3A is a diagram showing the artificial hip joint stem in FIG. 2, specifically a side view thereof as viewed from an arrowed direction A1 in FIG. 2.
Figure 3B:
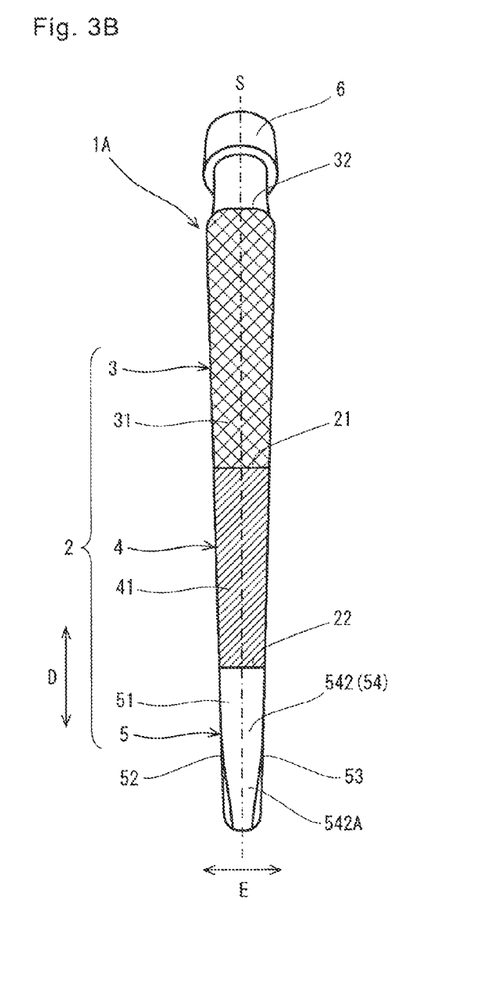
FIG. 3B is a side view thereof as viewed from an arrowed direction B1 in FIG. 2.

As shown in FIGS. 3A and 3B, the central axis S in the present embodiment is also a configuration allowing a midpoint in a thickness direction E at the stem distal part 5 to be continuously obtained along the longitudinal direction D of the stem body 2. In the present embodiment, both the first boundary part 21 and the second boundary part 22 are substantially perpendicular to the central axis S of the stem body 2 even in a view other than the front view.

In the present embodiment, as shown in FIG. 2, L1 to L3 have a relationship of L1:L2:L3=1:0.4 to 1:0.3 to 0.9, where L1 is a length of the stem proximal part 3, L2 is a length of the stem intermediate part 4, and L3 is a length of the stem distal part in the front view.

The phrase "length L1 of the stem proximal part 3" denotes a distance between a straight line X1 and a straight line X2 in the front view. The phrase "straight line X1" denotes the straight line that is orthogonal to the central axis S and passes through a proximal lateral end portion 3a located closer to and located outside of a proximal portion of the stem proximal part 3. The phrase "straight line X2" denotes the straight line that is orthogonal to the central axis S and passes through an lateral end portion 2a in a boundary part of the stem proximal part 3 and the stem intermediate part 4. The straight line X2 in the present embodiment corresponds to a virtual extension line of the first boundary part 21.

The phrase "length L2 of the stem intermediate part 4" denotes a distance between the straight line X2 and a straight line X3 in the front view. The phrase "the straight line X3" denotes the straight line that is orthogonal to the central axis S and passes through an lateral end portion 2b in a boundary part of the stem intermediate part 4 and the stem distal part 5. The straight line X3 in the present embodiment corresponds to a virtual extension line of the second boundary part 22.

The phrase "length L3 of the stem distal part 5" denotes a distance between the straight line X3 and a straight line X4 in the front view. The phrase "the straight line X4" denotes the straight line that is orthogonal to the central axis S and passes through a distal end portion 5a of the stem distal part 5.

From the viewpoint of improving the stem insertability, the present embodiment includes the following configuration. That is, the lateral side surface 542 has the inclined surface 542A. The inclined surface 542A of the present embodiment is located closer to the distal end portion 542a of the lateral side surface 542 and is inclined so as to approach the medial side surface 541 as going toward the distal end portion 542a in the front view. In the present embodiment, the distal end portion 5a of the stem distal part 5 has a curved line shape in the front view. Further in the present embodiment, at least the stem distal part 5 has a tapered shape. The phrase "tapered shape" denotes that the member gradually decreases both in width and thickness toward the front end thereof. In the present embodiment, not only the stem distal part 5 but also the entirety of the stem body 2 has a gently tapered shape.

Figure 4A:
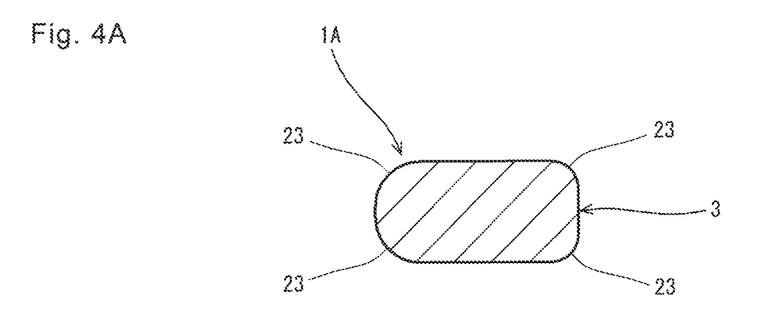
FIG. 4A is a diagram showing the artificial hip joint stem in FIG. 2, specifically an enlarged sectional view thereof taken along a line a1-a1 in FIG. 2.
Figure 4B:
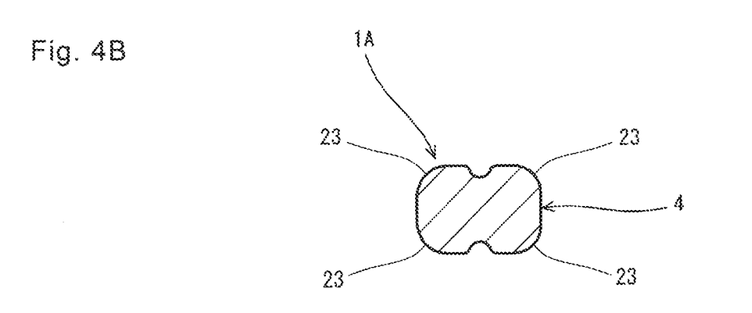
FIG. 4B is an enlarged sectional view thereof taken along a line b1-b1 in FIG. 2.

The foregoing stem 1A of the present embodiment is a so-called European stem. Therefore, as shown in FIGS. 4A and 4B, at least the stem proximal part 3 and the stem intermediate part 4 have a substantially rectangular shape in a cross-sectional configuration perpendicular to the central axis S in the present embodiment. According to this configuration, four corners of the cross-sectional configuration are contacted with the medullary cavity of the femoral bone 100, and the stem 1A can be supported from four directions in a well-balanced manner, thus achieving cementless fixation of the stem 1A to the proximal part 101 of the femoral bone 100. Additionally, the above configuration permits bone tissue preservation. That is, in a medullary cavity filled type stem that is one of conventional cementless stems, it is necessary to remove a large amount of cancellous bone because a stem having an approximately the same thickness as the medullary cavity is implanted therein. On the contrary, according to the foregoing configuration, the thickness of the stem 1A can be reduced than that of the medullary cavity, and the bone tissue can be preserved by decreasing the amount of removal of the cancellous bone.

Figure 4C:
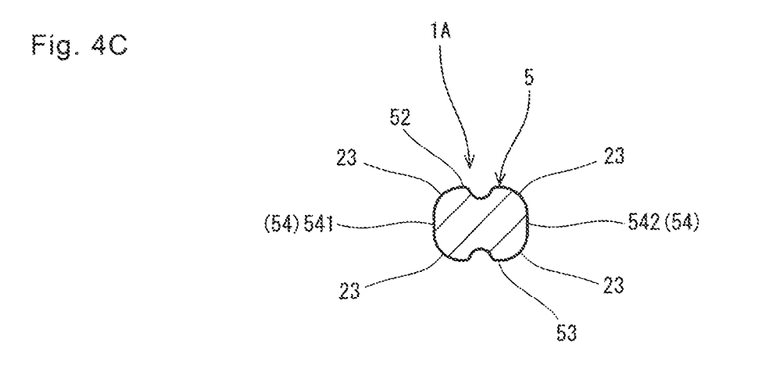
FIG. 4C is an enlarged sectional view taken along a line c1-c1 in FIG. 2.

The stem body 2 of the present embodiment further includes curved corners 23 obtained by round chamfering the corners of the foregoing cross-sectional configuration. According to this configuration, the four curved corners 23 located at the four corners of the cross-sectional configuration are individually contacted with the medullary cavity of the femoral bone 100, and the stem 1A can be supported from the four directions in the well-balanced manner. In the present embodiment, as shown in FIG. 4C, at least a portion of the stem distal part 5 located closer to the stem intermediate part 4 also has a substantially rectangular shape in the foregoing cross-sectional configuration, and the curved corners 23 are respectively located at four corners thereof. In the present embodiment, the curved corners 23 are formed by round chamfering, but not limited to this. The corners 23 may be beveled edges formed by chamfering.

On the other hand, the stem 1A of the present embodiment further includes a neck part 6 extending from the proximal end portion 32 of the stem proximal part 3 as shown in FIGS. 2, 3A and 3B. Examples of materials constituting the stem 1A are titanium alloy or cobalt-chrome alloy.

As described above, the stem 1A of the present embodiment is the member constituting the artificial hip joint 10 shown in FIG. 1. The artificial hip joint 10 of the present embodiment includes, besides the foregoing stem 1A, an artificial femoral head 11 fitted into the neck part of the stem 1A, and a socket 12 that slidably houses the artificial femoral head 11 and is fixed to an acetabulum 111 of a hipbone 110.

The artificial femoral head 11 of the present embodiment has a substantially spherical shape and includes a bottomed cylindrical shaped concave part 11a located at a bottom middle part thereof. The artificial femoral head 11 is fitted into the neck part 6 of the stem 1A with the concave part 11a interposed therebetween. Examples of materials constituting the artificial femoral head 11 are metals, such as cobalt-chrome alloy, or ceramics, such as alumina and zirconia.

The socket 12 of the present embodiment has a substantially cup shape and includes a substantially semispherical-shaped concave part 12a located at a bottom middle part thereof. The socket 12 slidably houses the artificial femoral head 11 in the concave part 12a. Examples of materials constituting the socket 12 are synthetic resins, such as polyethylene resin.

(Second Embodiment)

Figure 5:
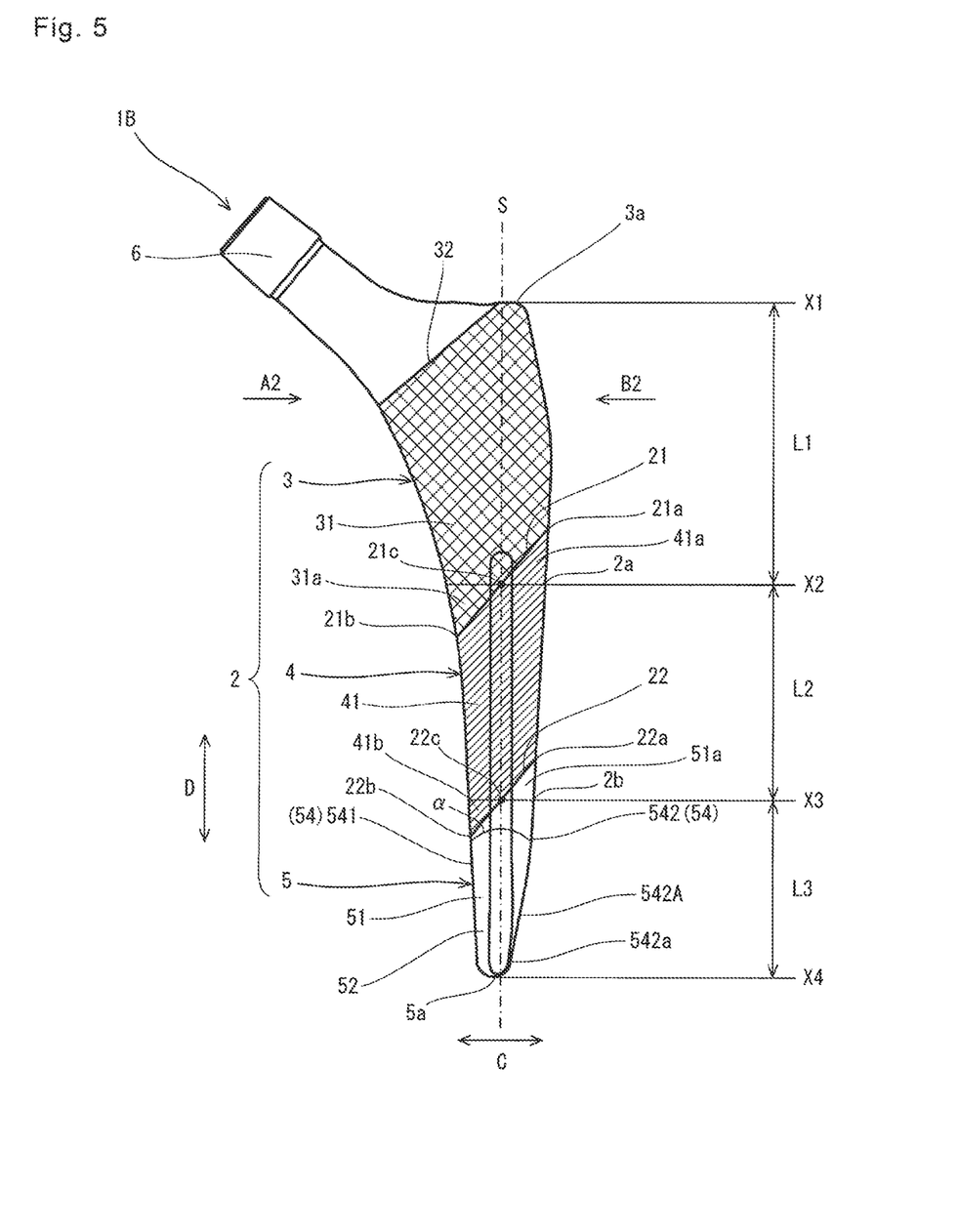
FIG. 5 is an enlarged front view showing an artificial hip joint stem according to a second embodiment of the present invention.
Figure 6A:
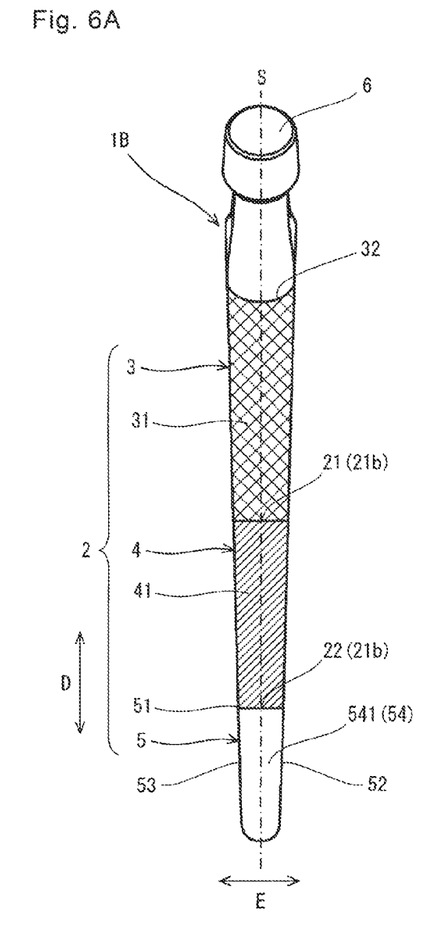
FIG. 6A is a diagram showing the artificial hip joint stem in FIG. 5, specifically a side view thereof as viewed from an arrowed direction A2 in FIG. 5.
Figure 6B:
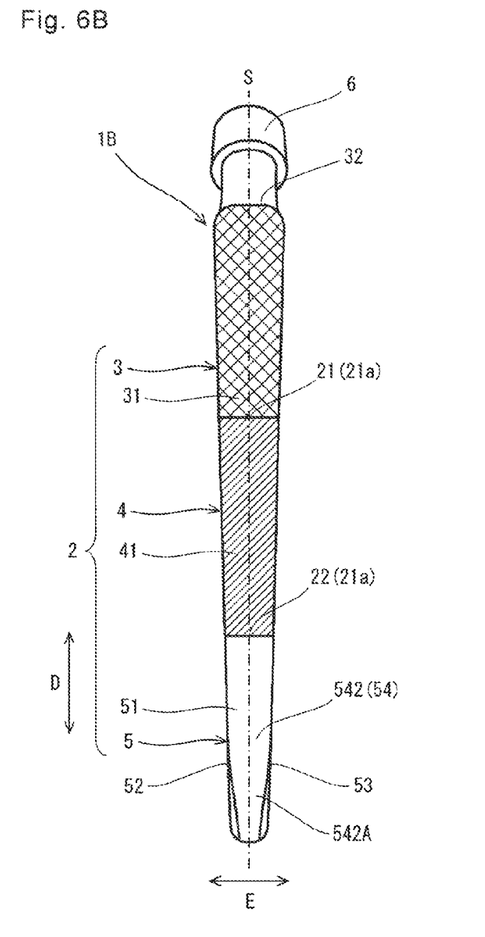
FIG. 6B is a side view thereof as viewed from an arrowed direction B2 in FIG. 5.

A stem and an artificial hip joint according to a second embodiment of the present invention are described in details below with reference to FIGS. 5, 6A and 6B. In FIGS. 5, 6A and 6B, the same components as those in FIGS. 1 to 4C are identified by the same reference numerals and the description thereof is generally omitted.

The present embodiment differs from the foregoing first embodiment in configuration of a first boundary part 21 of a rough surface 31 and a smooth satin surface 41 as well as a second boundary part 22 of the smooth satin surface 41 and a shiny surface 51. Specifically, as shown in FIG. 5, both of the first boundary part 21 and the second boundary part 22 in the stem 1B of the present embodiment are respectively inclined counterclockwise around points 21c and 22c located on a central axis S with respect to a reference line substantially perpendicular to the central axis S, namely, straight lines X2 and X3 in a front view.

More specifically, the first boundary part 21 is inclined around the point 21c on the basis of the straight line X2 so that an lateral end portion 21a of opposite end portions of the first boundary part 21, which is located on an lateral side, is located on a proximal side than an medial end portion 21b located on an medial side in the front view. Similarly, the second boundary part 22 is inclined around the point 22c on the basis of the straight line X3 so that an lateral end portion 22a of opposite end portions of the second boundary part 22, which is located on the lateral side, is located on the proximal side than an medial end portion 22b located on the lateral side in the front view. According to these configurations, as shown in FIGS. 5, 6A and 6B, both the lateral end portion 21a of the first boundary part 21 and the lateral end portion 22a of the second boundary part 22 are located on a more proximal side, consequently improving strength of the stem 1B.

In the present embodiment, the first boundary part 21 and the second boundary part 22 are parallel to each other. Further in the present embodiment, the point 21c is located at the intersection of the central axis S and the straight line X2, and the point 22c is located at the intersection of the central axis S and the straight line X3.

In the present embodiment, most of the rough source 31 need to be located at a stem proximal part 3, and part of the rough surface 31 may reach a stem intermediate part 4. Similarly, most of the smooth satin surface 41 need to be located at a stem intermediate part 4, and part of the smooth statin surface 41 may reach the stem proximal part 3 or a stem distal part 5. Most of the shiny surface 51 need to be located at the stem distal part 5, and part of the shiny surface 51 may reach the stem intermediate part 4.

In the present embodiment, a portion 31a of the rough surface 31 located on a distal side and an medial side extends from the stem proximal part 3 to the stem intermediate part 4. A portion 41a of the smooth satin surface 41 located on a proximal side and an lateral side extends from the stem intermediate part 4 to the stem proximal part 3. A portion 41b of the smooth satin surface 41 located on the distal side and the medial side extends from the stem intermediate part 4 to the stem distal part 5. A portion 51a of the shiny surface 51 located on the proximal side and the lateral side extends from the stem distal part 5 to the stem intermediate part 4.

FIG. 5 shows a state that the stem 1B is implanted in the left leg. When the stem 1B is implanted in the right leg, the first boundary part 21 and the second boundary part 22 are respectively inclined clockwise around the points 21c and 22c with respect to the straight lines X2 and X3.

Other configurations are similar to those in the stem 1A and the artificial hip joint 10 according to the foregoing first embodiment, and hence the description thereof is omitted.

(Third Embodiment)

A stem and an artificial hip joint according to a third embodiment of the present invention are described in details below with reference to FIGS. 7 to 9C. In FIGS. 7 to 9C, the same components as those in FIGS. 1 to 6B are identified by the same reference numerals and the description thereof is generally omitted.

Figure 7:
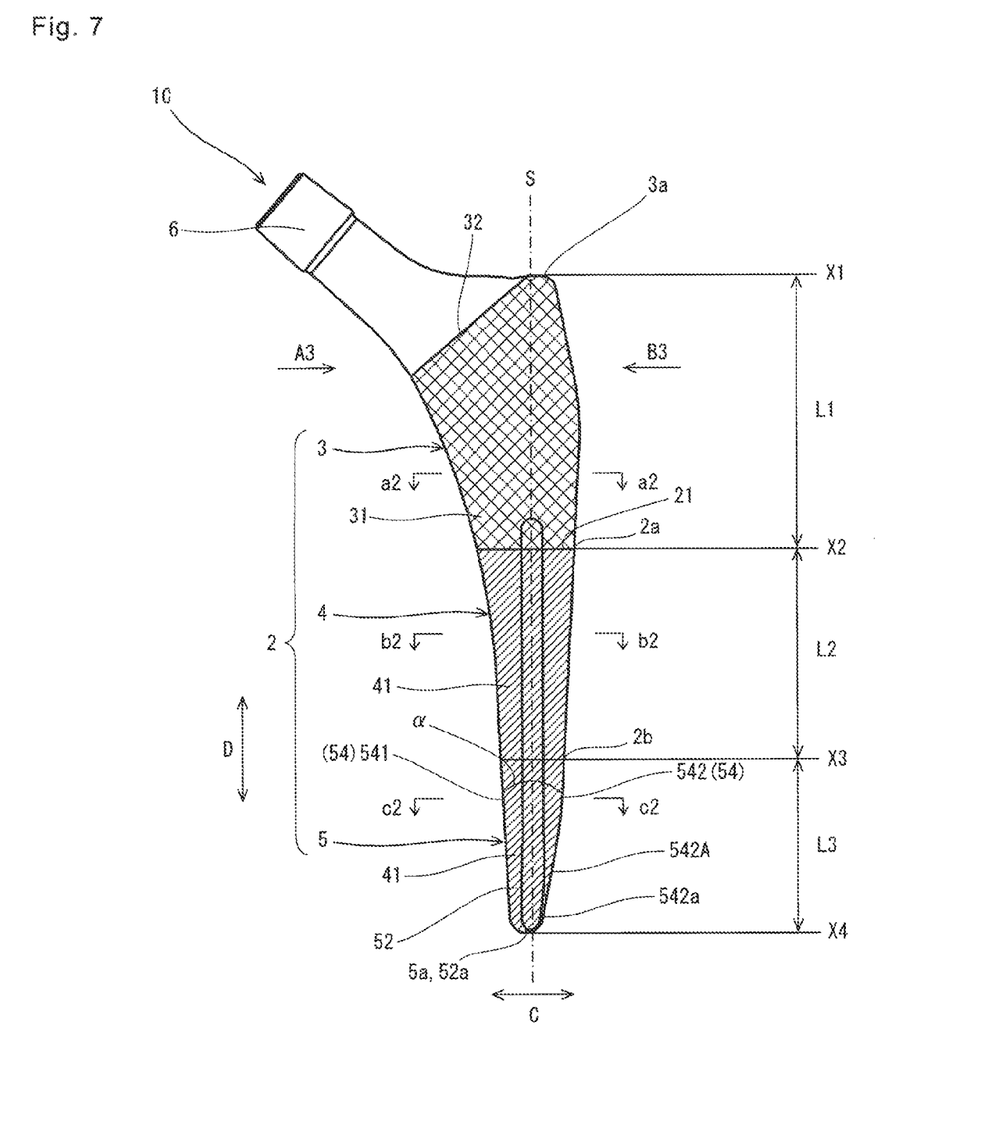
FIG. 7 is an enlarged front view showing an artificial hip joint stem according to a third embodiment of the present invention.
Figure 8A:
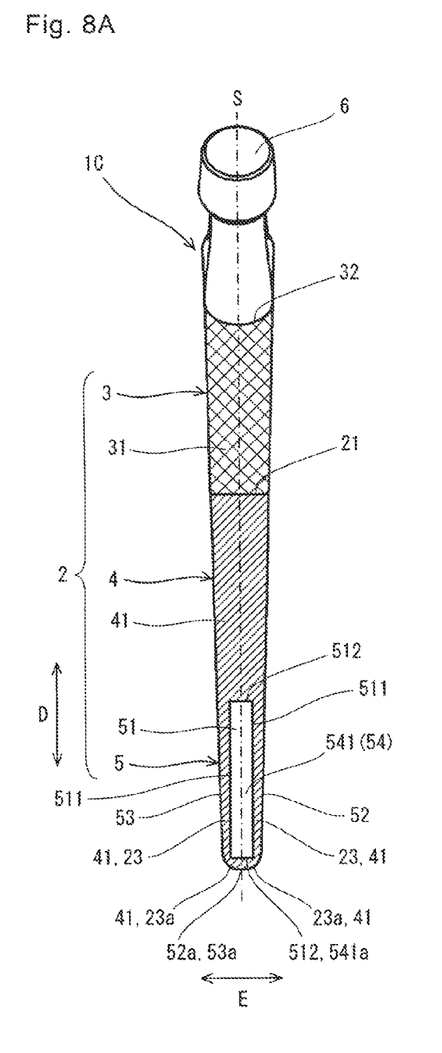
FIG. 8A is a diagram showing the artificial hip joint stem in FIG. 7, specifically a side view thereof as viewed from an arrowed direction A3 in FIG. 7.
Figure 8B:
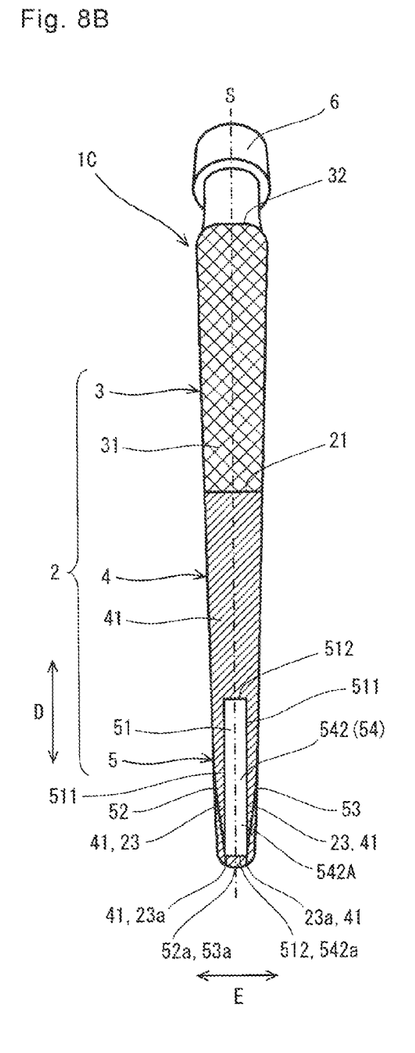
FIG. 8B is a side view thereof as viewed from an arrowed direction B3 in FIG. 7.

The present embodiment differs from the foregoing first embodiment in position of the shiny surface 51. Specifically, in the stem 1C of the present embodiment, the shiny surface 51 is located on an medial side surface 541 and an lateral side surface 542 of a stem distal part 5 as shown in FIGS. 7, 8A and 8B. Further in the stem 1C of the present embodiment, a smooth satin surface 41 extends from the stem intermediate part 4 to distal end portions 52a and 53a of a front surface 52 and a rear surface 53 of the stem distal part 5, respectively.

These configurations also produce effects similar to those of the stem 1A according to the foregoing first embodiment. That is, by disposing the shiny surface 51 at the medial side surface 541, the bone ongrowth is difficult to occur at the stem distal part 5, and it is capable of preventing the stem distal part 5 from being fixed to the femoral bone 100, thereby making it possible to reduce the occurrence of thigh pain and stress shielding. Additionally, by disposing the shiny surface 51 at the lateral side surface 542, it is capable of preventing the stem distal part 5 from being contacted with soft tissue and cancellous bone at a proximal part 101 of a femoral bone 100 when inserting the stem 1C, and consequently exhibiting excellent stem insertability.

From the viewpoint of well-balanced attainment of the effect owing to the shiny surface 51 in the present embodiment, the shiny surface 51 has a substantially rectangular shape having a pair of long sides 511 and 511 substantially parallel to a central axis S and a pair of short sides 512 and 512 substantially perpendicular to the central axis S.

Further in the present embodiment, as described above, the smooth satin surface 41 exists in a large area because it extends to the distal end portions 52a and 53a of the front surface 52 and the rear surface 53, respectively. Hence, the present embodiment achieves large improvement in rotary resistance force of the stem 1C.

Figure 9A:
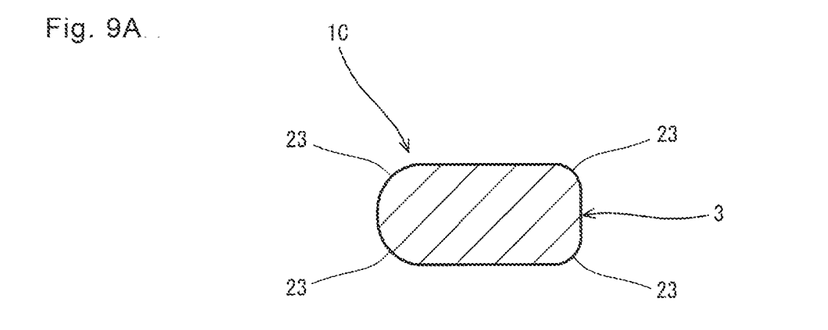
FIG. 9A is a diagram showing the artificial hip joint stem in FIG. 7, specifically an enlarged sectional view thereof taken along a line a2-a2 in FIG. 7.
Figure 9B:
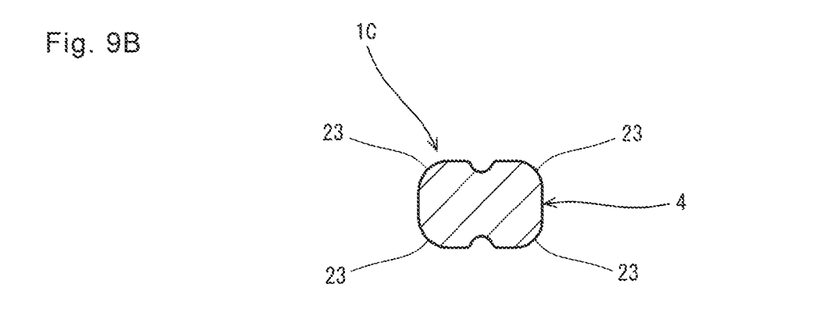
FIG. 9B is an enlarged sectional view thereof taken along a line b2-b2 in FIG. 7.
Figure 9C:
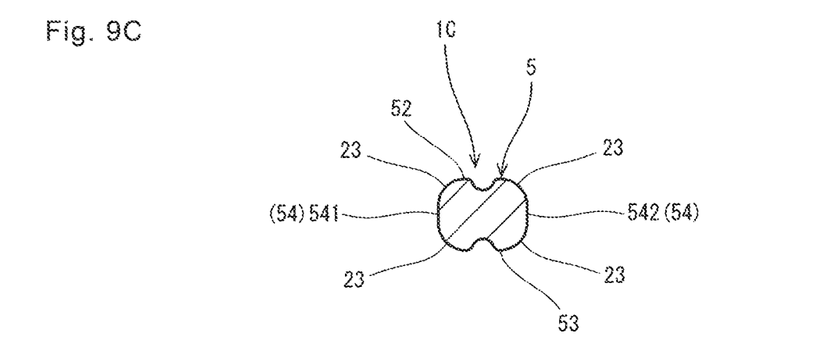
FIG. 9C is an enlarged sectional view taken along a line c2-c2 in FIG. 7.

From the viewpoint of improving the rotary resistance force of the stem 1C, the present embodiment includes the following configuration. That is, as shown in FIG. 9C, the stem distal part 5 of the present embodiment has a substantially square shape (substantially rectangular shape) in a cross-sectional configuration perpendicular to the central axis S. The stem body 2 of the present embodiment further includes curved corners 23 obtained by round chamfering the corners of the foregoing cross-sectional configuration. As shown in FIGS. 8A and 8B, the smooth satin surface 41 of the present embodiment extends from the stem intermediate part 4 to distal end portions 23a of the curved corners 23.

In the present embodiment, the front surface 52 and the rear surface 53 are continuous with each other at their respective distal end portions 52a and 53a. In the present embodiment, the shiny surface 51 located on the medial side surface 541 and the shiny surface 51 located on the lateral side surface 542 are spaced apart from each other with the smooth satin surface 41 interposed therebetween.

The shiny surface 51 of the present embodiment needs to be located at least over the circumferences of the distal end portions 541a and 542a of the medial side surface 541 and the lateral side surface 542, respectively. When the shiny surface 51 is located only over the circumferences of the distal end portions 541a and 542a, the smooth satin surface 41 needs to be located in the remaining region of each of the medial side surface 541 and the lateral side surface 542.

Other configurations are similar to those in the stems 1A and 1B and the artificial hip joint 10 according to the foregoing first or second embodiment, and hence the description thereof is omitted.

(Fourth Embodiment)

Figure 10:
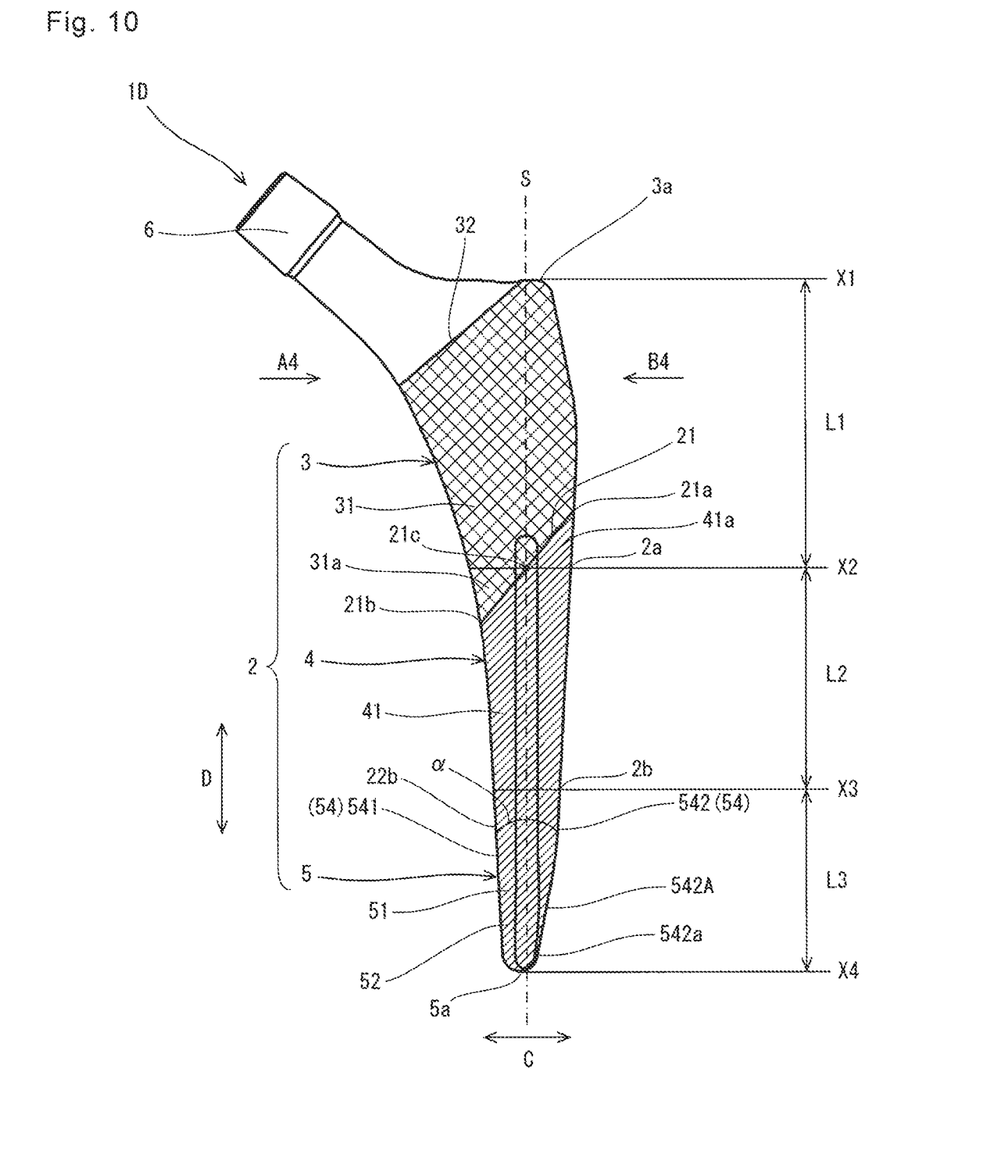
FIG. 10 is an enlarged front view showing an artificial hip joint stem according to a fourth embodiment of the present invention.
Figure 11A:
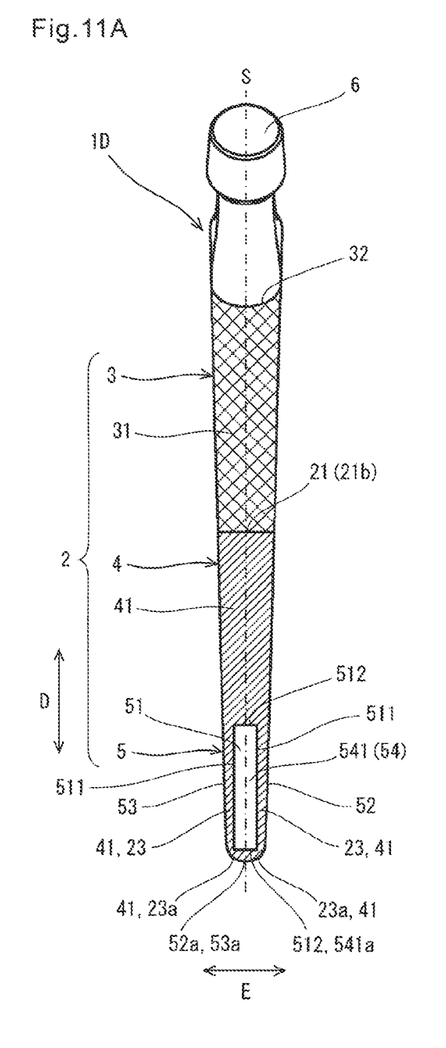
FIG. 11A is a diagram showing the artificial hip joint stem in FIG. 10, specifically a side view thereof as viewed from an arrowed direction A4 in FIG. 10.
Figure 11B:
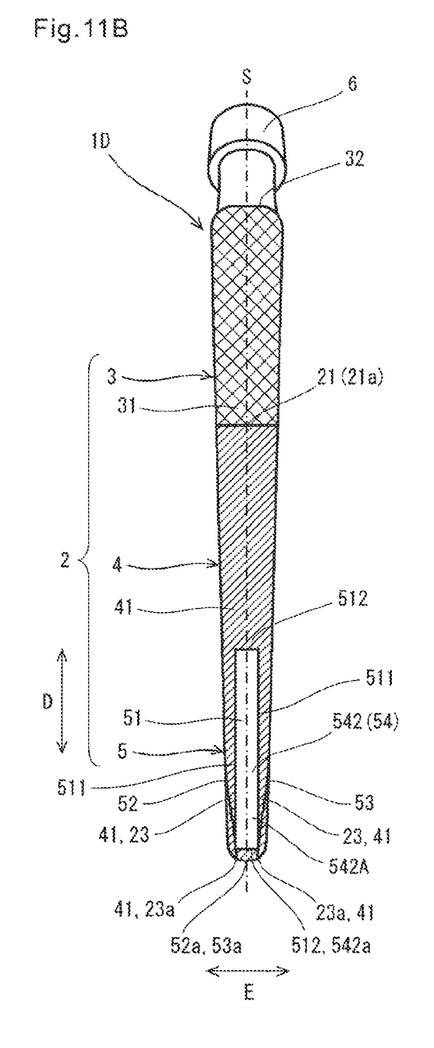
FIG. 11B is a side view thereof as viewed from an arrowed direction B4 in FIG. 10.

A stem and an artificial hip joint according to a fourth embodiment of the present invention are described in details below with reference to FIGS. 10, 11A and 11B. In FIGS. 10, 11A and 11B, the same components as those in FIGS. 1 to 9C are identified by the same reference numerals and the description thereof is generally omitted.

The present embodiment differs from the foregoing third embodiment in that a shiny surface 51 located on an medial side surface 541 and the shiny surface 51 located on an lateral side surface 542 have different shapes from each other. Specifically, in the stem 1D of the present embodiment, the length of the shiny surface 51 located on the lateral side surface 542 is longer than the length of the shiny surface 51 located on the medial side surface 541 as shown in FIGS. 10, 11A and 11B. This configuration achieves large improvement in effect obtained by disposing the shiny surface 51 on the lateral side surface 542, namely, the stem insertability.

Other configurations are similar to those in the stems 1A to 1C and the artificial hip joint 10 according to the foregoing first, second or third embodiment, and hence the description thereof is omitted.

While the several embodiments of the present invention have been illustrated and described, it is to be understood that the present invention is not limited to the foregoing embodiments, but many modifications and changes can be made without departing from the spirit and scope of the present invention.

For example, according to the foregoing second embodiment, both the first boundary part 21 and the second boundary part 22 are inclined. Alternatively, one of the first and second boundary parts 21 and 22 may be inclined. That is, the stem 1B can be configured so that at least one of the first and second boundary parts 21 and 22 is inclined.

Additionally, the configurations of the stems 1A to 1D according to the foregoing respective embodiments may be combined with each other. For example, the configuration of the first boundary part 21 of the stem 1D according to the fourth embodiment may be changed to the configuration of the first boundary part 21 according to the stem 1A of the first embodiment or the stem 1C of the third embodiment. That is, the first boundary part 21 of the stem 1D according to the fourth embodiment may be substantially perpendicular to the central axis S of the stem body 2 in the front view.

What is claimed is:

1. An artificial hip joint stem, comprising:
   A stem body divided into a stem proximal part adapted to be located toward a femur end, a stem distal part adapted to be located toward a medial position in a femur, and a stem intermediate part located between the stem proximal part and the stem distal part,
   the stem body comprises
   a first surface located over an entire circumference of the stem proximal part and having a surface roughness (Ra) of 10-80μm,
   a second surface located over an entire circumference of the stem intermediate part and having a surface roughness (Ra) of 0.1-1.0μm, and
   a third surface located at the stem distal part and having a surface roughness (Ra) of less than 0.1μm,
   wherein the stem body further comprises
   a front surface, a rear surface and side surfaces each being located at the stem distal part,
   the side surfaces comprise a medial side surface and a lateral side surface opposed to each other,
   the third surface is located on the medial side surface and the lateral side surface, and the second surface extends from the stem intermediate part to a distal end of each of the front surface and the rear surface in areas located between and adjoining to the third surface on the medial side surface and the lateral side surface.

2. The artificial hip joint stem according to claim 1, wherein the stem proximal part has a length L1 which is a distance between a first straight line (X1) that is orthogonal to a central axis of the stem body and passes through a proximal lateral end portion of the stem proximal part and a second straight line (X2) that is orthogonal to the central axis and passes through a lateral end portion in a boundary part of the stem proximal part and the stem intermediate part, the stem intermediate part has a length L2 which is a distance between the second straight line (X2) and a third straight line (X3) that is orthogonal to the central axis and passes through a lateral end portion in a boundary part of the stem intermediate part and the stem distal part, and the stem distal part has a length L3 which is a distance between the third straight line (X3) and a fourth straight line (X4) that is orthogonal to the central axis and passes through a distal end portion of the stem distal part, and L1 to L2 to L3 have a relationship of L1:L2:L3=1:0.4 to 1:0.3 to 0.9.

3. The artificial hip joint stem according to claim 1, wherein the stem body further comprises
   a medial side surface and a lateral side surface located at the stem distal part and opposed to each other,
   the lateral side surface comprises an inclined surface located closer to a distal end portion of the lateral side surface than a boundary between the stem intermediate part and the stem distal part and inclined so as to approach the medial side surface in a direction toward the distal end portion of the lateral side surface.

4. The artificial hip joint stem according to claim 1, wherein a distal end portion of the stem distal part is curved.

5. The artificial hip joint stem according to claim 1, wherein at least the stem proximal part and the stem intermediate part have a rectangular shape in a cross-sectional configuration perpendicular to a central axis of the stem body,
   wherein the stem body further comprises
   chamfered parts obtained by round chamfering corners of the cross-sectional configuration.

6. The artificial hip joint stem according to claim 1, wherein the third surface has a rectangular shape comprising a pair of first sides parallel to a central axis of the stem body and a pair of second sides perpendicular to the central axis, and the second sides are shorter than the first sides.

7. The artificial hip joint stem according to claim 1, wherein
   the stem distal part has a square shape with chamfered corners in a cross-sectional configuration perpendicular to a central axis of the stem body, the chamfered corners are obtained by round chamfering of the corners of the cross-sectional configuration, and the second surface extends from the stem intermediate part to a distal end portion of each of the chamfered corners.

8. The artificial hip joint stem according to claim 1, wherein the front surface and the rear surface are continuous with each other at their respective distal end portions, and the third surface located on the medial side surface and the third surface located on the lateral side surface are spaced apart from each other with the second surface interposed therebetween.

9. The artificial hip joint stem according to claim 1, further comprising:

a neck part extending from a proximal end portion of the stem proximal part.

* * * * *